US00PP20622P3

(12) United States Plant Patent
Layt

(10) Patent No.: US PP20,622 P3
(45) Date of Patent: Jan. 5, 2010

(54) *LIRIOPE MUSCARI* PLANT NAMED 'LIRF'

(50) Latin Name: *Liriope muscari*
Varietal Denomination: LIRF

(76) Inventor: Todd Anthony Layt, P.O. Box 1011, Richmond NSW (AU), 2753

( * ) Notice: Subject to any disclaimer, the term of this patent is extended or adjusted under 35 U.S.C. 154(b) by 82 days.

(21) Appl. No.: 12/077,553

(22) Filed: Mar. 20, 2008

(65) Prior Publication Data

US 2008/0235838 P1 Sep. 25, 2008

Related U.S. Application Data

(60) Provisional application No. 60/919,717, filed on Mar. 23, 2007.

(51) Int. Cl.
*A01H 5/00* (2006.01)

(52) U.S. Cl. ..... Plt./450

(58) Field of Classification Search ..... Plt./450
See application file for complete search history.

*Primary Examiner*—Annette H Para

(57) ABSTRACT

'LIRF' is a distinctive variety of *Liriope muscari* which is characterized by the combination of its narrow leaf width, dense foliage and a pink flower color.

2 Drawing Sheets

Latin name of the genus and species:

The Latin name of the genus and species of the novel variety disclosed herein is *Liriope muscari.*

Variety denomination:

The inventive variety of *Liriope* disclosed herein has been given the variety denomination 'LIRF'.

BACKGROUND OF THE INVENTION

The present invention relates to a new and distinct perennial variety of *Liriope muscari,* which has been given the variety denomination of 'LIRF'. Its market class is that of an ornamental plant. 'LIRF' is intended for use in landscaping and as a decorative plant.

The *Liriope muscari* variety 'LIRF' was finally selected in 2005 in an Australian nursery in the state of New South Wales following a selection process carried out from 2002 to 2005 involving approximately 20000 seedlings of *Liriope muscari* cultivar 'Big Blue' (unpatented) production stock. 'LIRF' is a seedling selection from open pollinated *Liriope muscari* cultivar 'Big Blue'. 'LIRF' was selected due to its narrow leaf width combined with dense foliage and a pink flower color. 'LIRF' was first propagated asexually by division in the state of New South Wales, Australia and has since been asexually propagated by division and micropropagation. The distinctive characteristics of the inventive 'LIRF' variety are stable from generation to generation; clones of the variety produced by asexual reproduction maintain the distinguishing characteristics of the original plant.

'LIRF' has an upright growth habit with a very dense shoot density whereas 'Big Blue' has a semi upright growth habit and a medium shoot density. 'LIRF' has a narrow leaf width resulting in finer looking foliage whereas 'Big Blue' has a broad leaf width. 'LIRF' has a pink flower color whereas 'Big Blue' has a light purple to lilac flower color.

An application for plant breeders' rights for variety 'LIRF' has been lodged with the Australian Plant Breeders' Rights Office, and was first gazetted in Mar. 27, 2006 under Application No. 2006/038.

SUMMARY OF THE INVENTION

'LIRF' is a distinctive variety of *Liriope muscari* which is characterized by the combination of its narrow leaf width, dense foliage and a pink flower color.

BOTANICAL DESCRIPTION OF THE PLANT

The following is a detailed botanical description of a new and distinct variety of a *Liriope muscari* ornamental plant known as 'LIRF'. Plant observations were made on plants grown in New South Wales, Australia. Unless indicated otherwise, the descriptions disclosed herein are based upon observations made in February 2006 of mature 'LIRF', 24 months old, plants grown in nursery pots.

Those skilled in the art will appreciate that certain characteristics will vary with older or, conversely, younger plants. 'LIRF' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1995 edition. Note that generic color descriptions such as 'pink' do not exist in the R.H.S. charts and the corresponding R.H.S. colors are quoted.

'LIRF' is a perennial *Liriope muscari* plant which is a seedling selection from a *Liriope muscari* cultivar 'Big Blue'. After its selection, 'LIRF' was asexually propagated by division and then by micropropagation. 'LIRF' has a green leaf color and pink flowers displayed within the foliage.

These features and other characteristics are apparent from the description provided below.

Growth Habit, Dimensions and Color

Figure 1:
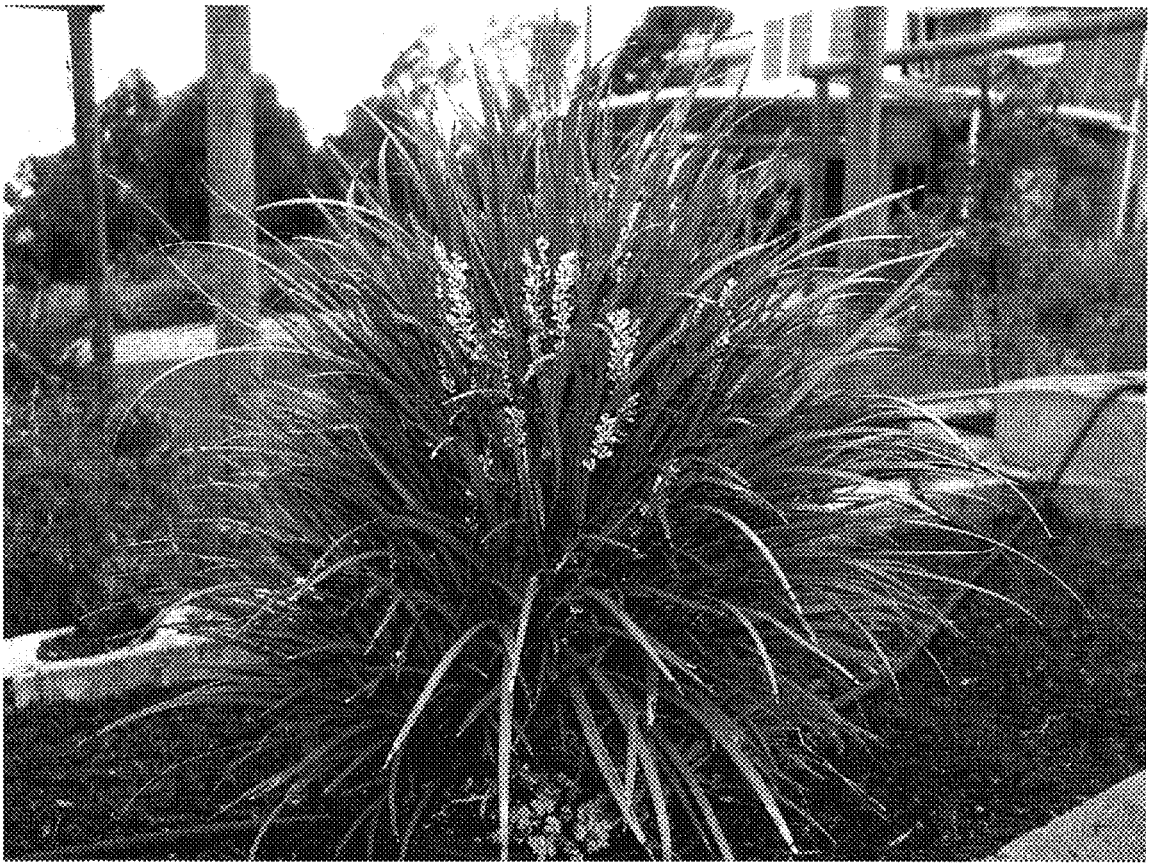
FIG. 1 shows a 'LIRF' plant.
Figure 2:
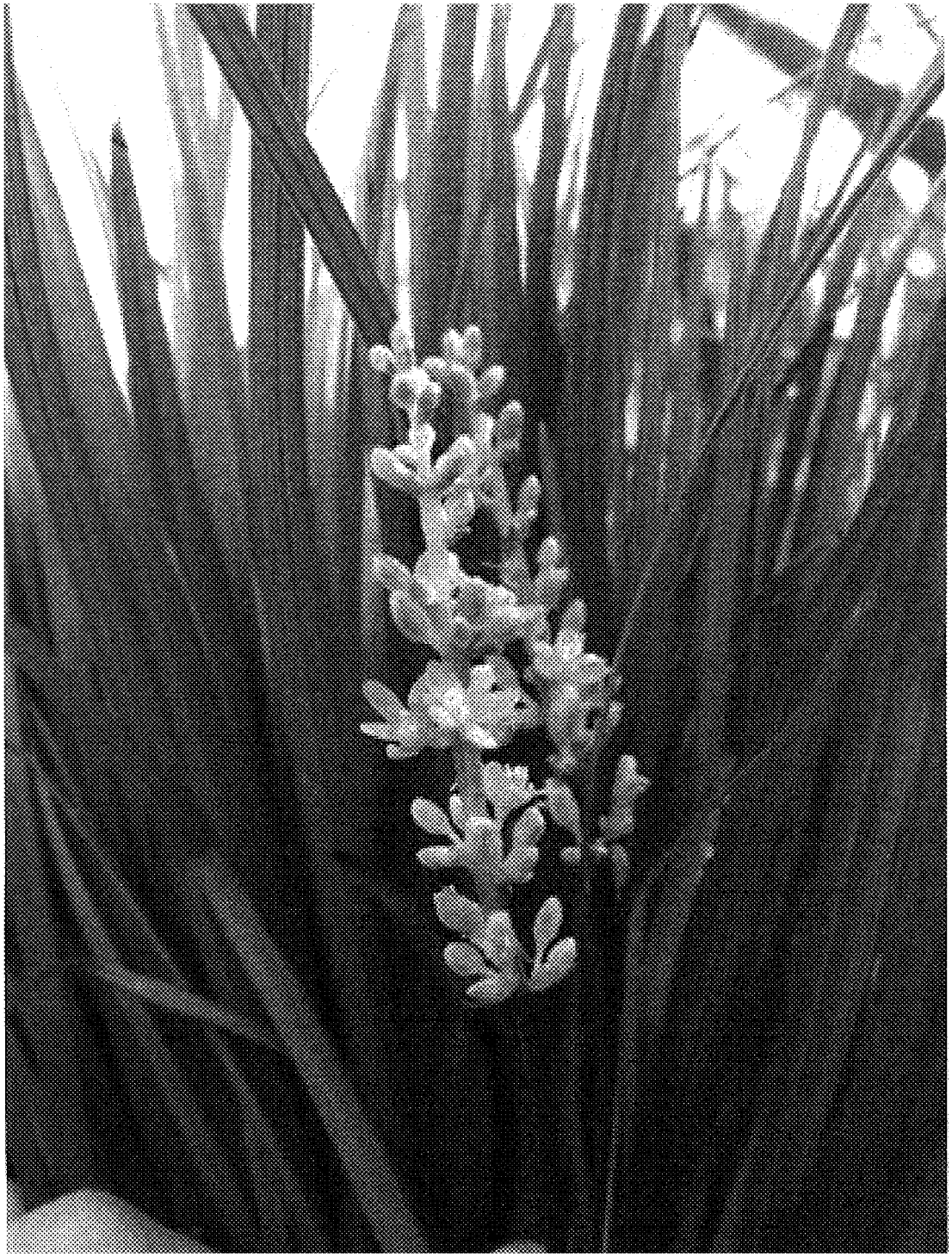
FIG. 2 shows an inflorescence of an 'LIRF' plant showing flower detail.

'LIRF' is a short-medium plant forming an upright clump with slightly spreading leaves. Average plant height is to 50–55 cm and average plant spread is 65–85 cm in a mature plant grown in a garden in Sydney, New South Wales, Australia (observed January 2007). A representative 'LIRF' plant is shown in FIG. 1. The upper side of the mature leaf is yellow green in color (observed January 2007) corresponding to approximately RHS 147A.

Leaf margins and mid ribs do not contrast prominently with the leaf blade. The leaf lower side color corresponds to the upper leaf side but has a less glossy surface texture. The leaf is generally 3–6 mm in width, and reaches an average length of 65–85 cm. The leaf shape is ligulate-ensiforn, leaf base is cauline, leaf margin is entire, leaf apex is acute and leaf surface texture is glossy and glabrous. The leaf venation pattern is parallel; the color is the same as the rest of the leaf. The leaf attitude is erect to semi erect with maturity.

Roots

The roots of 'LIRF' are colored white and fleshy and thick, similar to other *Liriope muscari*.

Inflorescence

The inflorescence is a raceme with flowers borne in clusters of typically 4 or 5 and reducing in number near the apex. Each flower cluster consists of pedicellate flowers ranging from a very short pedicel length (almost sessile) to up to 3.5 mm long. Inflorescence length is approximately 26 cm on average and the raceme position is within the foliage. Raceme length is 50–60 mm typically. Peduncle color is yellow green approximately RHS 146B. Each flower cluster is subtended by a small bract colored yellow green approximately RHS 146B. Pedicel color is purple RHS 78D. The flowering season in Sydney, NSW, Australia is late December-January until Late February.

Flowers

Flower bud color is violet approximately RHS 84D (immature) to RHS 86D (mature). Mature petal color is purple violet RHS 82C-D. Anthers are yellow RHS 6C and stigma is purple violet RHS 82D. Flower diameter is approximately 4–5 mm when fully opened.

Comparison of LIRF with Other Varieties of *Liriope muscari*

'LIRF' has a narrower leaf width and denser foliage than common *Liriope muscari*.

'LIRF' has a very narrow leaf width and very dense foliage whereas 'Big Blue' has a broad leaf width (11–12 mm) and medium density foliage. 'LIRF' has a short-medium plant height with short-medium leaf length whereas 'Big Blue' has a tall plant height (to 75 cm) with long leaf length. 'LIRF' has a 'pink' looking flower color corresponding to purple violet RHS 82C-D whereas 'Big Blue' has a flower color corresponding to violet RHS 86B.

'LIRF' differs from the variety 'Bigun' (U.S. Plant Pat. No. 15,474) as it has a shorter plant height, narrower leaf width, an absence of leaf twisting and pink flowers whereas 'Bigun' has a medium plant height (to 60 cm), broad leaf width (to 18 mm), leaf twisting present and dark violet colored flowers.

'LIRF' differs from the variety 'Samantha' (unpatented) as it has a more upright plant growth habit, a narrower leaf width and deeper pink flowers whereas 'Samantha' has a more semi-upright plant growth habit, a medium-broad leaf width (to 12 mm) and lighter pink colored flowers corresponding to purple RHS 78C.

The combination of its dense upright growth habit, very narrow leaf width and pink flower color makes 'LIRF' a desirable ornamental plant suited for mass production for pot and landscape use.

Asexual Reproduction

After its initial discovery, 'LIRF' was transplanted into a 140 mm pot for further trials and testing. After divisions were made for several subsequent generations, 'LIRF' was observed to retain color and size characteristics that were noted in the original 'LIRF' seedling. Divisions of 'LIRF' root within 2 to 3 weeks. 'LIRF' was divided into several pots for further evaluation. Potting mix used contained 50% sand and 50% peat. Plants were divided into 90 mm×50 mm×50 mm tubes.

'LIRF' has been propagated in vitro using micropropagation and has been observed to reproduce from generation to generation in a uniform and stable manner maintaining original color and size characteristics.

Environmental Tolerances

'LIRF' has typical shade tolerance for the species. The winter hardiness of 'LIRF' is at least to zone 8*a*–8*b* in the Southeastern United States, and evaluation of winter hardiness is ongoing. 'LIRF' has moderate to good drought tolerance. 'LIRF' has moderate to good recovery with watering after severe wilting. 'LIRF' does well in sandy soils, but also tolerates heavy, clay-type soils well.

Disease Resistance

'LIRF' has typical resistance to fungal and bacterial pathogens compared to other similar *Liriope muscari* cultivars.

That which is claimed is:

1. A new and distinct variety of *Liriope muscari* plant named 'LIRF', substantially as described and illustrated herein.

* * * * *